United States Patent
Nabeta et al.

(10) Patent No.: US 9,427,435 B2
(45) Date of Patent: *Aug. 30, 2016

(54) NARCOTIC EMULSION FORMULATIONS FOR TREATMENT OF CANCER PAIN

(71) Applicants: Teikoku Pharma USA, Inc., San Jose, CA (US); Techno Guard Co., Ltd., Kawasaki, Kanagwa (JP)

(72) Inventors: Kiichiro Nabeta, Tokyo (JP); Toru Hibi, Hyogo (JP)

(73) Assignees: Teikoku Pharma USA, Inc., San Jose, CA (US); Techno Guard Co., Ltd., Kawasaki, Kanagawa (JP)

( * ) Notice: Subject to any disclaimer, the term of this patent is extended or adjusted under 35 U.S.C. 154(b) by 28 days.

This patent is subject to a terminal disclaimer.

(21) Appl. No.: 14/492,509

(22) Filed: Sep. 22, 2014

(65) Prior Publication Data

US 2015/0141461 A1  May 21, 2015

Related U.S. Application Data

(62) Division of application No. 12/685,401, filed on Jan. 11, 2010, now Pat. No. 8,871,791.

(60) Provisional application No. 61/155,853, filed on Feb. 26, 2009.

(51) Int. Cl.
*A61K 31/4468* (2006.01)
*A61P 29/00* (2006.01)
(Continued)

(52) U.S. Cl.
CPC ......... *A61K 31/4468* (2013.01); *A61K 9/0019* (2013.01); *A61K 9/107* (2013.01); *A61K 47/10* (2013.01); *A61K 47/12* (2013.01); *A61K 47/24* (2013.01); *A61K 47/44* (2013.01)

(58) Field of Classification Search
CPC .. A61K 31/4468; A61K 47/10; A61K 47/24; A61K 9/0019; A61K 9/107
See application file for complete search history.

(56) References Cited

U.S. PATENT DOCUMENTS 4,647,586 A   3/1987  Mizushima et al.
7,211,596 B2  5/2007  Yoshida et al.
(Continued)

FOREIGN PATENT DOCUMENTS

CN   101066245   11/2007
CN   101199525    6/2008
(Continued)

OTHER PUBLICATIONS

Notification of the Second Office Action, China Patent Application No. 201080009143.9, mailed on Oct. 21, 2013, 6 pages.
(Continued)

*Primary Examiner* — Savitha Rao
(74) *Attorney, Agent, or Firm* — Bret E. Field; Brian E. Davy; Bozicevic, Field & Francis LLP

(57) ABSTRACT

Methods and compositions of treating a subject for cancer pain are provided. In the subject methods, a subject is treated for cancer pain by administering to the subject an effective amount of a narcotic emulsion, e.g., fentanyl elmulsion, formulation. In certain embodiments, the emulsion formulations include a narcotic active agent, oil, water and a surfactant. Also provided are methods of making the subject emulsion formulations as well as kits that include the emulsion formulations.

12 Claims, 7 Drawing Sheets

Daily Changes in Cancer Pain

(51) Int. Cl.
  *A61K 9/00*    (2006.01)
  *A61K 9/107*   (2006.01)
  *A61K 47/10*   (2006.01)
  *A61K 47/24*   (2006.01)
  *A61K 47/12*   (2006.01)
  *A61K 47/44*   (2006.01)

(56) References Cited

U.S. PATENT DOCUMENTS

| | | |
|---|---|---|
| 7,252,822 B2 | 8/2007 | Shelton et al. |
| 2003/0162775 A1 | 8/2003 | Singh et al. |
| 2005/0276763 A1 | 12/2005 | Pfeifer et al. |
| 2006/0111382 A1 | 5/2006 | Shafer et al. |
| 2006/0189682 A1 | 8/2006 | Payne et al. |
| 2007/0087977 A1 | 4/2007 | Robbins |
| 2007/0116729 A1 | 5/2007 | Palepu |
| 2007/0207207 A1 | 9/2007 | Tzannis et al. |
| 2007/0261695 A1 | 11/2007 | Kottayil et al. |
| 2009/0286832 A1 | 11/2009 | Nabeta et al. |

FOREIGN PATENT DOCUMENTS

| | | |
|---|---|---|
| CN | 101938963 | 1/2011 |
| EP | 0770387 A1 * | 10/1995 |
| JP | 1987-11915 | 5/1987 |
| JP | 2001519396 | 10/2001 |
| JP | 2004043479 | 2/2004 |
| JP | 2008505972 | 2/2008 |
| JP | 2011-509539 A | 7/2011 |
| JP | 2011-552037 A | 8/2012 |
| KR | 10-2011-0099747 A | 9/2011 |
| WO | WO9918967 | 4/1999 |
| WO | WO2006098241 | 9/2006 |
| WO | WO2006115690 | 11/2006 |
| WO | WO2007103185 | 9/2007 |
| WO | WO2008133952 | 11/2008 |
| WO | WO2009140059 | 11/2009 |

OTHER PUBLICATIONS

Higashi et al., Edaravone (3-methyl-1-phenyl-2-pyrazolin-5-one), a novel free radical scavenger, for treatment of cardiovascular diseases, Recent Pat Cardiovasc Drug Discov (2006), 1(1):85-93.

Jumma et al., Mixture experiments with the oil phase of parenteral emulsions, Eur J Pharm Biopharm (1998), 46(2):161-7.

Yokoyama et al., "FENTANYL." Pain Clinic vol. 26, (2005), Spring Supplement, pp. S166-S172.

Wang et al., Submicron lipid emulsion as a drug delivery system for nalbuphine and its prodrugs, J Control Release (2006), 115(2):140-9.

* cited by examiner

Cancer Pain Assay
Fentanest™ (Fentanyl Citrate Injection)

Cancer Pain Assay
Fentanyl Emulsion A

Duration of Straub's Tail Reaction Induced by Fentanest™ and Fentanyl Emulsion A Figures in the columns indicate the number of animals which show Straub's tail reaction. Six animals per group are given Fentanest or fentanyl emulsion A.

One-Direction Locomotor Activity Effect of Fentanest™ (Fentanyl Citrate Injection)

One-Direction Locomotor Activity Effect of Fentanyl Emulsion A

One-Direction Locomotor activity following Fentanest™ and Fentanyl Emulsion A

NARCOTIC EMULSION FORMULATIONS FOR TREATMENT OF CANCER PAIN

CROSS-REFERENCE TO RELATED APPLICATIONS

Pursuant to 35 U.S.C. §119 (e), this application claims priority to the filing dates of: U.S. Provisional Patent Application Ser. No. 61/155,853 filed on Feb. 26, 2009; the disclosure of which application is herein incorporated by reference.

INTRODUCTION

Pain can be defined as an unpleasant sensory and emotional experience associated with actual or potential tissue damage. It is a complex process influenced by both physiological and psychological factors. Pain is typically subjective and many health care professionals are not trained to effectively assess or treat pain.

Cancer pain, which can be caused by the disease itself or by treatments, is very common in people with cancer. Many people with cancer experience pain while undergoing treatment, and almost all people in the advanced stages of cancer experience pain.

Cancer pain may depend on many different factors, such as the type of cancer, the stage of the disease, the disease location, and a patient's tolerance for pain. Cancer pain can originate from the primary cancer itself or from other areas in the body where the cancer has spread (metastases). As a tumor grows, it may put pressure on nerves, bones or other organs, causing pain. Pain may also result from fracturing of bones, infection or inflammation associated with the disease. Cancer pain may not just arise from the physical effect of the cancer on a region of the body, but also may be caused by the chemicals that may be secreted from cancerous cells and/or tissues. The type of cancer pain may also vary. For example, it may be acute, chronic, or breakthrough pain. Cancer pain may also vary in the duration of each pain episode, its severity and frequency of its occurrence.

The two major classes of pharmaceutical drugs used to treat cancer pain are opioid analgesics, and non-steroidal anti-inflammatory drugs (NSAID). These classes of drug, are typically administered systemically. The systemic administration of drugs to relieve cancer pain is frequently inadequate. For example, systemic administration of opioids for cancer pain may cause nausea, the inhibition of bowel function, urinary retention, the inhibition of pulmonary function, cardiovascular effects, and sedation.

One opioid analgesic that has been employed for the treatment of cancer pain is fentanyl. Fentanyl is the generic name for the compound N-(1-phenethyl-4 piperidyl) propionanilide, a useful injectable analgesic. See U.S. Pat. No. 3,164,600. Fentanyl is an opioid agonist and shares many of the pharmacodynamic effects of opioids such as morphine and meperidine. However, compared to these opioids, fentanyl exhibits little hypnotic activity, rarely induces histamine release, and respiratory depression is more short-lived. Fentanyl is commercially available for intravenous, intrabuccal (lozenge-transmucosal) and transdermal administration.

Various injectable fentanyl formulations have been developed to date. One such formulation is a fentanyl citrate composition sold in the United States under the brandname SUBLIMAZE™ that comprises fentanyl citrate, USP water for injection, and sufficient sodium hydroxide to raise the pH to 6.5. A different fentanyl citrate composition has been sold in Europe under the brandname FENTANEST™ which consists only of fentanyl and USP water for injection without any deliberate pH adjustment.

Despite the utility of injectable fentanyl formulations, certain drawbacks of such formulations do exist. For example, injectable fentanyl formulations can cause unwanted central nervous system mediated side effects, such as respiratory depression, sedation and dizziness.

SUMMARY

Methods and compositions for treating a subject for cancer pain are provided. In the subject methods, a subject is treated for cancer pain by administering to the subject an effective amount of a narcotic emulsion, e.g., fentanyl elmulsion, formulation. In certain embodiments, the emulsion formulations include a narcotic active agent, oil, water and a surfactant. Also provided are methods of making the subject emulsion formulations as well as kits that include the emulsion formulations.

DEFINITIONS

Figure 1:
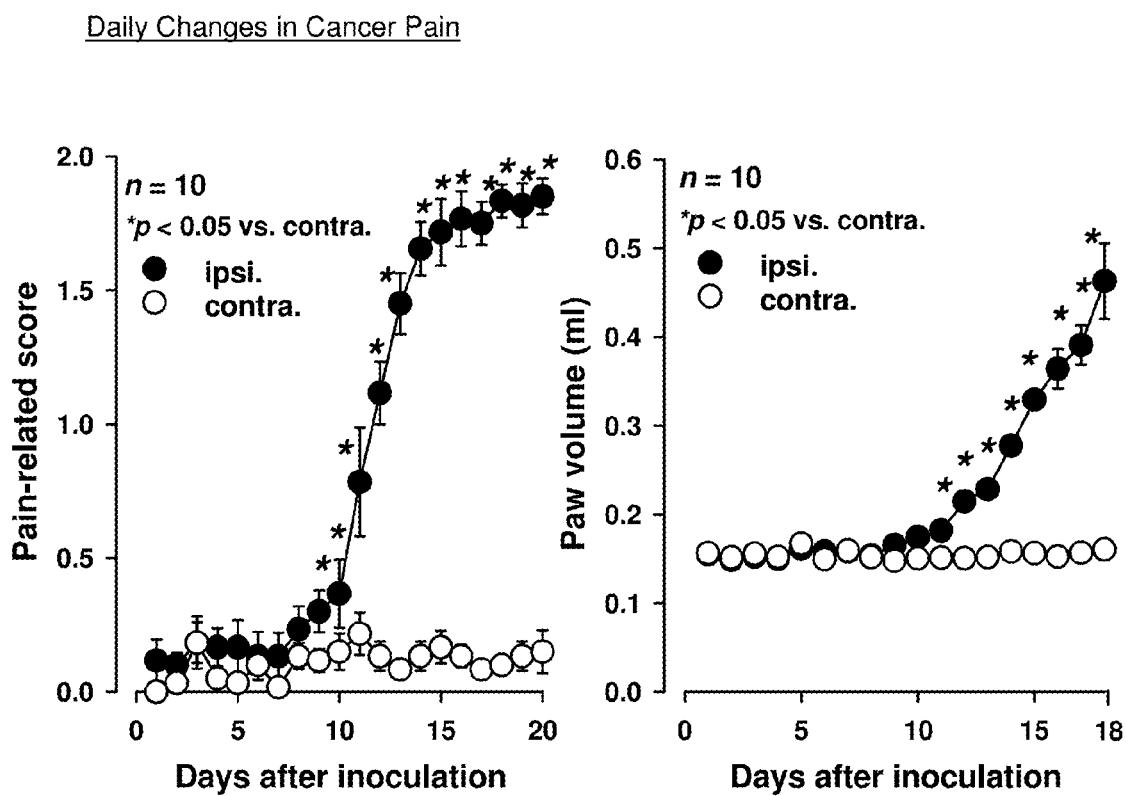
FIG. 1 shows the daily changes in cancer pain vs. days after melanoma cell inoculation in mice.

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

"Alkyl" refers to monovalent saturated aliphatic hydrocarbyl groups having up to 10 carbon atoms, or up to 9 carbon atoms, up to 8 carbon atoms, or up to 3 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "alkyl" also includes "cycloalkyls" as defined herein.

"Cycloalkyl" refers to cyclic hydrocarbyl groups having from 3 to 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like.

"Heterocycloalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of such heterocyclic non-aromatic rings include, but are not limited to, aziridinyl, azetidinyl, piperazinyl, and piperidinyl.

"Heteroaryl" refers to a stable heterocyclic aromatic ring and fused rings containing one or more heteroatoms independently selected from N, O and S. A fused heterocyclic ring system may include carbocyclic rings and need only include one heterocyclic ring. Examples of such heterocyclic aromatic rings include, but are not limited to, pyridine, pyrimidine, and pyrazinyl.

"Aryl" refers to a monovalent aromatic hydrocarbon group derived by the removal of one hydrogen atom from a single carbon atom of a parent aromatic ring system. Typical aryl groups include, but are not limited to, groups derived from benzene, ethylbenzene, mesitylene, toluene, xylene, aniline, chlorobenzene, nitrobenzene, and the like.

"Aralkyl" or "arylalkyl" refers to an alkyl group, as defined above, substituted with one or more aryl groups, as defined above.

"Halogen" refers to fluoro, chloro, bromo and iodo. In some embodiments, the halogen is fluoro or chloro.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryl, substituted thioaryl, thioketo, thiol, alkyl-S(O)—, aryl-S(O)—, alkyl-S(O)$_2$— and aryl-S(O)$_2$—.

DETAILED DESCRIPTION

Methods and compositions of treating a subject for cancer pain are provided. In the subject methods, a subject is treated for cancer pain by administering to the subject an effective amount of a narcotic emulsion, e.g., fentanyl elmulsion, formulation. In certain embodiments, the emulsion formulations include a narcotic active agent, oil, water and a surfactant. Also provided are methods of making the subject emulsion formulations as well as kits that include the emulsion formulations.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the subject invention, the methods and emulsion formulations employed therein are described first in greater detail, followed by a review of methods for preparing the formulations and kits that may include the formulations.

Methods of Treating Cancer Pain with Narcotic Emulsion Formulations

As summarized above, the invention provides methods of treating a subject for cancer pain. "Cancer pain" refers to pain arising or resulting from cancer, the destruction of tissue in any region associated with cancer or its metastases, pressure caused by cancer on bones, organs or nerves, infection or inflammation caused by the disease and chemicals secreted by cancerous cells and/or tissues. By cancer is meant a class of diseases involving neoplasia which include both cancers that involve a solid tumor and those that do not involve a solid tumor (e.g., leukemia). Cancer pain may also result from clinical procedures used to treat the disease (e.g., radiation therapy, chemotherapy, surgical intervention). As used herein, "cancer pain" does not include pain that occurs without cancer, complications arising from cancer or treatments employed to treat cancer. In some embodiments, cancer pain is internal or external pain. As used herein, "pain" includes nociception and the sensation of pain, and pain can be assessed objectively and subjectively, using pain scores and other methods, e.g., with protocols well-known in the art. Cancer pain, as used herein, includes allodynia (i.e., pain due to a stimulus that does not normally provoke pain) and hyperalgesia (i.e., increased response to a stimulus that is normally painful), which can in turn, be thermal or mechanical (tactile) in nature. In some embodiments, the pain is characterized by thermal sensitivity, mechanical sensitivity and/or resting pain. In some embodiments, the cancer pain comprises mechanically-induced pain or resting pain. In other embodiments, the cancer pain comprises resting pain. The pain can be primary or secondary pain, as is well-known in the art.

In practicing methods of invention, a narcotic emulsion formulation is parenterally administered to a subject. By "parenteral administration" is meant delivery by a protocol that delivers a quantity of a narcotic emulsion formulation to a subject, e.g., a patient suffering from cancer pain, by a route other than the digestive tract, e.g., via intramuscular injection, via intravenous delivery, etc. In certain embodiments, parenteral administration is by injection using an injection delivery device. The amount of narcotic emulsion formulation of the invention that is administered to the subject may vary depending on a number of factors, such as patient specifics, prior opiate treatment, nature of pain etc. In certain embodiments, the dosage that is administered per dosing event may range from 10 to 250 µg/dose, such as 10 to 150 µg/dose, including 25 to 100 µg/dose. Dosing guidelines for narcotic emulsion formulations already developed and followed by those of skill in the art may be employed with the subject formulations.

Narcotic emulsion formulations of the invention include a narcotic active agent. Narcotic active agents of interest are opioid receptor agonists. Opioid receptor agonists include opiates and opioids. "Opiates" and "Opioids" are roughly synonymous terms that generically denote a class of narcotic compounds characterized by having addiction-forming or addiction-sustaining properties similar to morphine or being capable of conversion into a drug having such addiction-forming or addiction-sustaining properties. Specifically, the term "opiates" denotes compounds containing the fundamental morphine or thebaine structure and possessing some affinity to any, or all, of the opioid receptor subtypes. Examples of opiates are heroin, buprenorphine, and naltrexone. An "opioid" is any compound, peptide or otherwise, which, while not containing the fundamental morphine or thebaine structure, possesses some affinity for any, or all, of the opioid receptor subtypes. A non-exclusive list of opiates and opioids includes mophine, heroin, opium, cocaine, fentanyl, ecgonine, thebaine. Commercially-available opiates and opioids (and exemplary trademarked names, where available) include: alfentanil (e.g., ALFENTA™ alfentanil hydrochloride injection), buprenorphine (e.g., SUBUTEX™ buprenorphine hexagonal orange sublingual tablet), carfentanil, codeine, dihydrocodeine, diprenorphine, etorphine, fentanyl (e.g., FENTANEST™ fentanyl citrate injection), heroin, hydrocodone (e.g., VICODIN™ hydrocodone bitartrate tablet), hydromorphone (e.g., DILAUDID™ hydromorphone hydrochloride oral liquid), LAAM (e.g., ORLAAM™ levomethadyl acetate oral liquid), levorphanol (e.g., LEVO-DROMORAN™ levorphanol tartrate), meperidine (e.g., DEMEROL™ meperidine hydrochloride), methadone (DOLOPHINE™ methadone hydrochloride tablets), morphine, naloxone (NARCAN™ naloxone hydrochloride injection), naltrexone (e.g., REVIA™ naltrexone hydrochloride tablet), beta-hydroxy 3-methylfentanyl, oxycodone (PERCODAN™ oxycodone hydrochloride tablet), oxymorphone (e.g., NUMORPHAN™ oxymorphone hydrochloride injection and NUMORPHAN™ oxymorphone hydrochloride suppository), propoxyphene (DARVON™ propoxyphene hydrochloride capsules and PULVULES™ propoxyphene hydrochloride capsules), remifentanil (ULTIVA™ remifentanil hydrochloride injection), sufentanil (e.g., SUFENTA™ sufentanil citrate injection), tilidine, and tramadol (ULTRAM™ tramadol hydrochloride tablet). The definition includes all opiates and opioids, from any source, including naturally-derived compounds, synthetic compounds, and semi-synthetic compounds. The definition also includes all isomers, stereoisomers, esters, ethers, salts, and salts of such isomers, steroeisomers, esters, and ethers, whenever the existence of such isomers, stereoisomers, esters, and ethers is possible within the specific chemical designation.

As the narcotic formulations employed in methods of the invention are emulsions, the formulations are liquid preparations that are a suspension of small globules of one liquid in a second liquid with which the first liquid will not mix. Emulsions in accordance with the present invention include a narcotic active agent oil, water and a surfactant.

An aspect of the emulsions employed in methods of the invention is that the emulsion includes an effective amount of a narcotic active agent. The amount of narcotic active agent in the emulsion may vary, and in certain embodiments ranges from 0.01 to 100 mg/ml, such as 0.1 to 50 mg/ml and including 0.1 to 10 mg/ml. In certain embodiments, the emulsion formulations employed in methods of the invention include an effective amount of fentanyl, i.e., N-(1-phenethyl-4 piperidyl) propionanilide. Fentanyl may be present in the formulation as the free base or a physiologically acceptable salt thereof, or a hydrate thereof. In certain embodiments, fentanyl is present in the composition at a concentration of 0.05 mg/ml or higher, including 0.1 mg/ml or higher, and in certain embodiments ranges from 0.1 to 10 mg/ml, such as 0.1 to 2 mg/ml, including 0.1 to 1 mg/ml.

Emulsion formulations of the invention are emulsions of water and oil. As the formulations are emulsions, they are mixtures of two immiscible (unblendable) fluids, where one fluid (an oil or water) (the dispersed phase) is dispersed in the other fluid (an oil or water) (the continuous phase). The combination ratio of the oil and the surfactant in the present invention is not particularly limited as long as a lipid emulsion can be obtained. The water present in the emulsions may be any convenient water, including deinionized water, water for injection (WFI), etc.

Also present in the subject emulsion formulations is an oil phase. Oils of interest are physiologically acceptable and include, but are not limited to: simple lipids, derived lipids, complex lipids that are derived from natural vegetable oil and fat, animal oil and fat, and mineral oil, or a mixture of those. In certain embodiments, the oil is chosen from soybean oil, olive oil, sesame oil, castor oil, corn oil, peanut oil, safflower oil, grape seed oil, eucalyptus oil, medium-chain fatty acid ester, and low-chain fatty acid ester. Animal oils and fat of interest include, but are not limited to, cod-liver oil, seal oil, sardine oil, docosahexiaenoic acid, and eicosapentaenoic acid. Mineral oils of interest include, but are not limited to, liquid paraffins. One or a combination of more than one of these can be used. Soybean oil, olive oil, and sesame oil are employed in certain embodiments. Highly refined oils and fats are employed in certain embodiments. Soybean oil and olive oil are employed in certain embodiments. In general, the amount of oil in the formulation composition should be 0.05 to 200 mg/ml, such as 1 to 200 mg/ml and including 10 to 100 mg/ml.

Also present in the subject emulsion formulations is a surfactant. Surfactants to be used for the present invention include any type of surfactant that has been used for pharmaceutical formulations, including, phospholipids, nonionic surfactants, or a mixture of such agents. Refined phospholipids, such as egg-yolk lecithin and soybean lecithin are employed in certain embodiments. Refined phospholipids may include phosphatidylinocytol, phosphatidyl ethanolamine, phosphatidylserine, and sphingomyeline with phosphatidylcholine as a main ingredient. Nonionic surfactants of interest include, but are not limited to, polyethylene glycol, polyoxyalkylene copolymer, and sorbitan fatty acid ester. One or a combination of more than one of these surfactants can be used. In certain embodiments, a refined surfactant is employed. A refined or hydrogenated phospholipid derived from egg-yolk or soybean with phosphatidylcholine as a main ingredient is employed in certain embodiments. The amount of surfactant may vary, ranging in certain embodiments from 0.1 to 50 mg/ml, such as 0.1 to 25 mg/ml.

Certain embodiments of the formulations also include one or more emulsification enhancers. Any type of fatty acid that has been used for pharmaceutical formulations can be used as an emulsification enhancer. Of interest are fatty acids with the carbon number of from 6 to 22, either natural or synthetic, and either saturated fatty acids or unsaturated fatty acids can be used, including but not limited to stearic acid, oleic acid, linoleic acid, palmitic acid, linolenic acid, and myristic acid. Refined fatty acids, e.g., oleic acid, are employed in certain embodiments. In certain embodiments, the amount of emulsification enhancer ranges from 0.1 to 10 mg/ml, such as from 1 to 5 mg/ml.

The emulsion formulations have a physiologically acceptable pH. In certain embodiments, the pH of the formulations ranges from 3 to 8, such as from 5 to 7.5. In certain embodiments, a pH adjusting agent is also present. pH adjusting agents of interest include, but are not limited to: sodium hydroxide, hydrochloric acid, phosphoric acid buffer solution, and citric acid buffer solution. The pH of the emulsion of the present invention can be adjusted at around 5.5 to 7.5 by using the pH adjusting agent.

Other additives that may be present in the formulation, as desired (e.g., stabilizing agents), include but are not limited to: glycerin, propylene glycol, polyethylene glycol (mainly less than the average molecular weight of 400), D-glucose, and maltose. When present, such agents may be present in an amount ranging from 0.1 to 50 mg/ml, such as 1 to 25 mg/ml.

Figure 2:
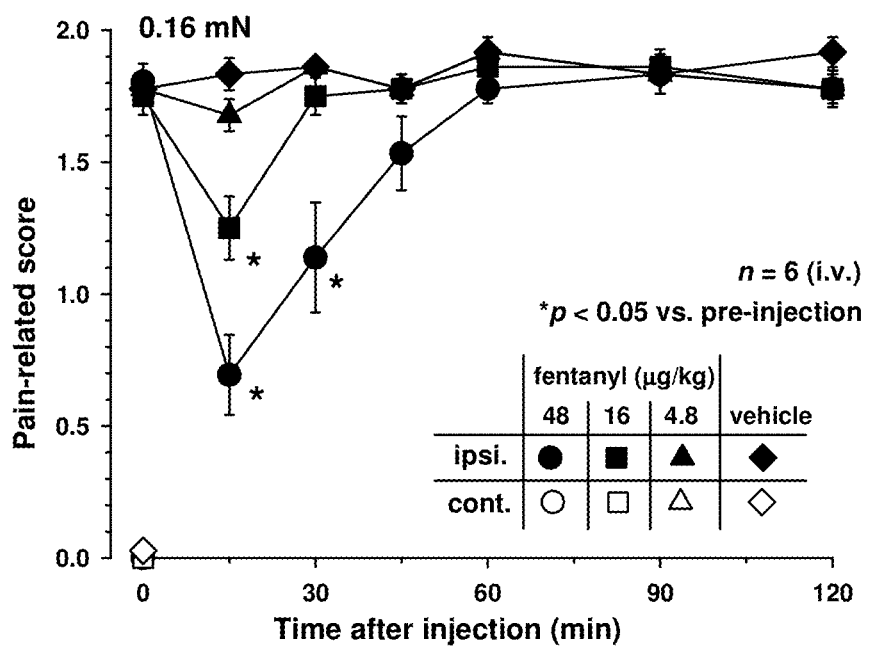
FIG. 2 shows the effects of FENTANEST™ fentanyl citrate injection formulation on pain-related scores vs. time in mice.
Figure 3:
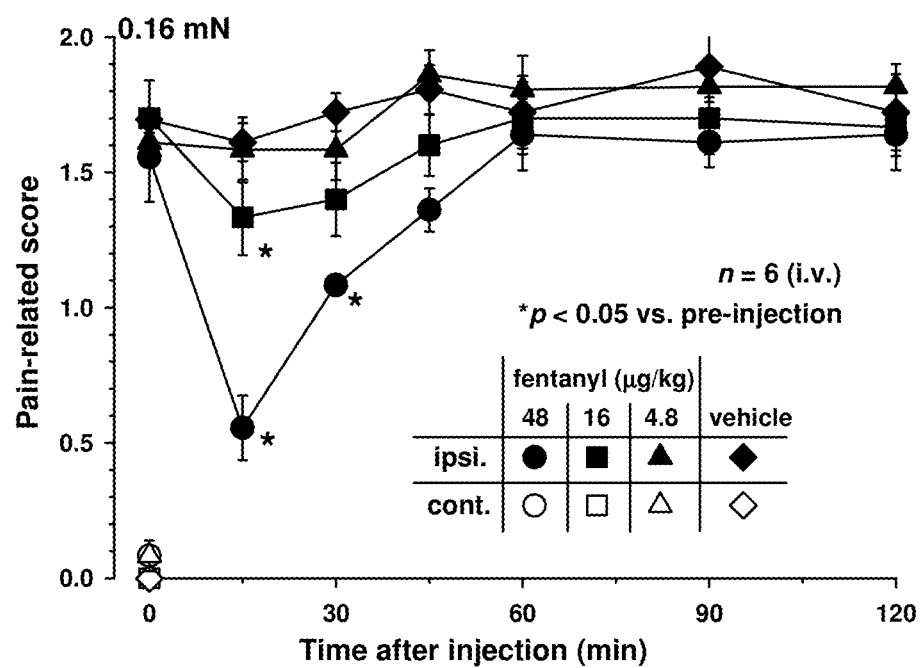
FIG. 3 shows the effects of fentanyl emulsion A on pain-related scores vs. time in mice.

Fentanyl containing emulsion formulations of the invention exhibit increased efficacy as compared to FENTANEST™ fentanyl citrate injection formulation 0.1 mg/2 ml (available from Sankyo Corporation, Tokyo, Japan), as illustrated by fentanyl emulsion A reported in the Experimental section below. Of interest in certain embodiments are emulsions, such as Fentanyl emulsion A, which are considered to exhibit greater efficacy than FENTANEST™ fentanyl citrate injection formulation if it is found that pain intensity (pain-related score) is suppressed by 61% and 68% at a dose of 48 µg/kg 15 min after FENTANEST™ fentanyl citrate injection formulation and the emulsion of the invention, e.g., fentanyl emulsion A, respectively, as illustrated in FIGS. 2 and 3.

Figure 4:
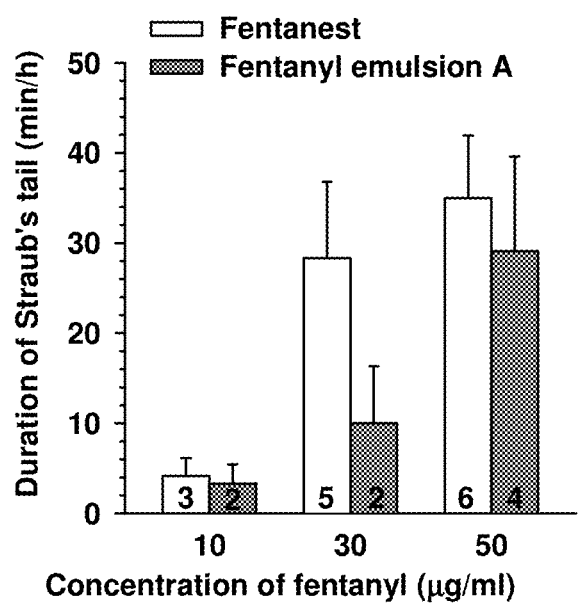
FIG. 4 shows the duration of Straub's tail reaction induced by FENTANEST™ fentanyl citrate injection formulation and fentanyl emulsion A. Preparations were administered intravenously in a volume of 0.10 ml. Straub's tail response was observed for 1 hour after administration and duration of the response was summed. Results shown are mean±SEM of animals which showed the response. The number of animals is shown in the columns.

The emulsion formulations of the invention exhibit reduced central nervous system mediated side effects as compared to a FENTANEST™ fentanyl citrate injection formulation. A formulation is considered to exhibit reduced central nervous system mediated side effects as compared to FENTANEST™ fentanyl citrate injection formulation if the incidence of Straub's tail, which is mediated by the action of fentanyl on the spinal cord, in a population of at least 6 mice following administration of a 30 µg/ml dose as illustrated in Table 3 below is 50% or less, such as 33% or less, as determined using the assay protocol reported in the experimental section, below. In mice showing Straub's tail response following a 30 µg/ml dose, the response duration following administration of fentanyl emulsion A is 36% of that of FENTANEST™ fentanyl citrate injection formulation, as illustrated in FIG. 4.

Figure 7:
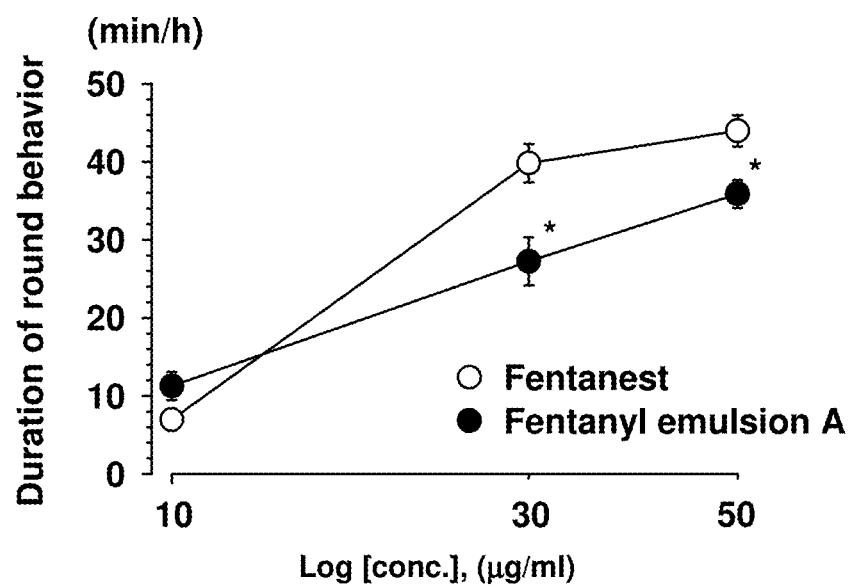
FIG. 7 shows a comparison of one-direction locomotor activity induced by FENTANEST™ fentanyl citrate injection formulation and fentanyl emulsion A. Results shown are mean±SEM of six animals. *p<0.05 (Dunnett's multiple comparisons).

A formulation is also considered to exhibit reduced brain mediated side effects, increase in locomotor activity, as compared to FENTANEST™ fentanyl citrate injection formulation. The duration of round behavior following administration of a 30 µg/ml dose is 40 and 27 min in FENTANEST™ fentanyl citrate injection formulation and fentanyl emulsion A groups, respectively, as illustrated in FIG. 7, as determined using the assay protocol reported in the experimental section, below.

In certain embodiments, the formulations are storage-stable. By storage-stable is meant that the compositions may be stored for extended periods of time without significant phase separation and/or significant reduction in activity of the active agent. In certain embodiments, the subject compositions are stable for 3 years or longer, etc., when maintained at 25° C. By the phrase "without substantially decreasing the activity of the active agent" is meant that at the end of the storage period, there is less than about 10% reduction in activity of the active agent compared to the beginning of the storage period.

The subject formulations and methods find use in a variety of applications, including preventing or treating cancer pain. By treatment is meant that at least an amelioration of the symptoms associated with the condition afflicting the subject is achieved, where amelioration is used in a broad sense to refer to at least a reduction in the magnitude of a parameter, e.g. symptom such as pain, associated with the condition being treated. As such, treatment also includes situations where the pathological condition, or at least symptoms associated therewith, are completely inhibited, e.g., prevented from happening, or stopped, e.g., terminated, such that the subject no longer suffers from the condition, or at least the symptoms that characterize the condition.

Accordingly, the present invention is useful for treating, delaying development of and/or preventing cancer pain in individuals including all mammals, both human and non-human, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects, e.g., patients, are humans. Moreover, the present invention is useful in individuals having pain associated with cancer, the destruction of tissue in any region associated with cancer or its metastases, pressure caused by cancer on bones, organs or nerves, infection or inflammation caused by the disease and chemicals secreted by cancerous cells and/or tissues. By cancer is meant a class of diseases involving neoplasia which include those cancers that involve a solid tumor and those that do not involve a solid tumor (e.g., leukemia).

Accordingly, in one aspect, the invention provides methods of treating cancer pain in an individual comprising administering an effective amount of an emulsion of a narcotic active agent. In some embodiments, the cancer pain comprises one or more of: allodynia, hyperalgesia, mechanically-induced pain, thermally-induced pain, thermally induced pain, mechanically induced pain, or resting pain. In some embodiments, the cancer pain comprises mechanically-induced pain and/or resting pain. In other embodiments, the cancer pain comprises resting pain. The pain can be primary and/or secondary pain. In other embodiments, allodynia is suppressed, ameliorated and/or prevented, and in some embodiments, hyperalgesia is suppressed, ameliorated and/or prevented. In still further embodiments, allodynia and/or hyperalgesia is thermal or mechanical (tactile) in nature (or both), or resting pain. In some embodiments, the pain is chronic pain. In other embodiments, the pain is breakthrough cancer pain.

In another aspect, the invention provides methods of ameliorating and/or preventing the development or progression of cancer pain. In some embodiments, the emulsion is administered during and/or after the onset of cancer pain. In one embodiment, the emulsion is administered 1 hour, 2 hours, 3 hours, 4 hours, 6 hours, 8 hours, 12 hours, 24 hours, 30 hours, 36 hours, or more, after the onset of cancer pain.

In another aspect, the invention provides methods for increasing pain threshold. As used herein, "increasing pain threshold" refers to a reduction, diminishment and/or minimization of pain associated with cancer, the destruction of tissue in any region associated with cancer or its metastases, pressure caused by cancer on bones, organs or nerves, infection or inflammation caused by the disease and chemicals secreted by cancerous cells and/or tissues (including reduced, diminished, and/or minimized subjective perception of pain). By cancer is meant a class of diseases involving neoplasia which include those cancers that involve a solid tumor and those that do not involve a solid tumor (e.g., leukemia). In yet another aspect, the invention provides methods for enhancing recovery from each cancer pain episode.

In certain embodiments, methods of the invention include a diagnostic step. Individuals may be diagnosed as being in need of the subject methods using any convenient protocol, and are generally known to be in need of the subject methods, e.g., they are suffering from a target disease condition or have been determined to be at risk for suffering from a target disease condition, prior to practicing the subject methods.

Diagnosis or assessment of pain is well-established in the art. Assessment may be performed based on objective measure, such as observation of behavior such as reaction to stimuli, facial expressions and the like. Assessment may also be based on subjective measures, such as patient characterization of pain using various pain scales. See, e.g., Katz et al, Surg Clin North Am. (1999) 79 (2):231-52; Caraceni et al. J Pain Symptom Manage (2002) 23(3):239-55.

Pain relief may also be characterized by time course of relief. Accordingly, in some embodiments, pain relief is subjectively or objectively observed after 1, 2, or a few hours (and in some embodiments, peaks at about 12-18 hours). In another embodiment, pain relief is subjectively or objectively observed at 24, 36, 48, 60, 72 or more hours following the event associated with cancer pain.

Preparation Methods

The emulsion formulations of the invention can be prepared using any convenient protocol. In one embodiment, an injection solvent, e.g., WFI, is added to a smooth mixture of a suitable oil. After the mixture is roughly emulsified, it is then finely emulsified, e.g., by using a high pressure emulsification machine. For rough emulsification, Homomixer (Mizuho Industrial Co., Ltd.) or High Flex Disperser (SMT) can be used. For fine emulsification, a high pressure homogenizer such as Gaulin Homogenizer (APV-SMT) and Microfluidizer (Microfluidics) can be used. In case of using a high pressure homogenizer, the emulsion may be run through 2 to 50 times, such as 5 to 20 times, with a pressure of approximately 500 to 850 kg/cm$^2$. The procedure of mixing and emulsifying can be carried out at room temperature or at a temperature lower than room temperature. In certain embodiments, the above preparation is made with nitrogen gas.

Kits

Also provided are kits that find use in practicing the subject methods, as described above. For example, kits for practicing the subject methods may include a quantity of the emulsion composition, present in unit dosages, e.g., ampoules, or a multi-dosage format. As such, in certain embodiments the kits may include one or more unit dosages (e.g., ampoules) of the emulsion formulation. In yet other embodiments, the kits may include a single multi dosage amount of the emulsion formulation.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

I. Fentanyl Emulsion Formulation & Preparation

A. Formulation
(Emulsion 250 ml)

TABLE 1

| Ingredients for the oil phase | |
| --- | --- |
| | Emulsion A |
| Soybean Oil | 25 g |
| Refined Egg-Yolk Phospholipid | 4.5 g |
| Oleic Acid | 0.6 g |

TABLE 2

| Ingredients for the aqueous phase (Glycerin solution) | |
| --- | --- |
| | Emulsion A |
| Glycerin | 5.52 g |
| Purified Water | 200 ml |

B. Procedure

Ingredients for the oil phase were added to a beaker and heated to 60° C. while stirring at 7,000 rpm to dissolve the ingredients. 25 mg of Fentanyl was added and stirred. (The process took approximately 10 minutes.) 50 ml of the glycerin solution was added in drops into the mixture and stirred at 10,000 rpm for 10 minutes. The solution was transferred into a separable flask. The remaining glycerin solution was added while stirring at 12,000 rpm in an emulsion machine for 30 minutes. Purified water was added to make the total volume of the emulsion 250 ml. The emulsion was emulsified 20 times while cooling the mixture at a pressure of 650 bar with a high pressure emulsion machine, LAB-1000 (APV, Denmark). (No adjustment was needed if the pH of the emulsion is between 6 and 7. If the pH was not between 6 and 7, the pH was adjusted with hydrochloric acid solution or sodium hydroxide solution. No adjustment was made in this experiment as the pH was between 6.3 and 6.7.) After high-pressure emulsification, the emulsion was filtered (pore size of 0.4 μm) and the emulsion was added into ampoules while adding $N_2$ gas. The ampoules were sterilized by autoclave sterilization (121° C. for 10 minutes). After sterilization, the ampoules were cooled and stored.

II. Cancer Pain Assay of Fentanyl Formulation

The analgesic effects of FENTANEST™ fentanyl citrate injection formulation and fentanyl emulsion A (produced as described in I. above) were examined for cancer pain in mice.

A. Materials and Methods

Animals

Male C57BL/6Cr mice were used.

Test Preparations

1) FENTANEST™ fentanyl citrate injection formulation (fentanyl citrate, 0.1 mg/2 ml fentanyl)

2) Fentanyl emulsion A (0.1 mg/ml fentanyl; average particle size=181 nm)

Administration

Each formulation was prepared with appropriate solvent. Each formulation was injected intravenously in an amount of 0.05 ml per 10 g body weight.

Preparation of Cancer Pain Model

B16-BL6 melanoma cells were used in the experiment. The cells were cultured in modified Eagle's minimal essential medium (MEM) containing 10% fetal bovine serum. The cells were prepared to have $2 \times 10^5$ cells/20 μl and they were intraplantar injected (i.pl.) to the back of the hind paw of the mouse by using the low dose injection syringe with 29G needle (Becton, Dickinson and Company).

Analgesic Examination

The reaction to the mechanical stimuli to the hind paw was used as an index. The von Frey filament (North Coast Medical, San Jose, USA) with the strength of 0.16 mN was used for the measurement. After applying the von Frey filament to the back of the hind paw, the reaction was categorized into three stages (0=no reaction; 1=move away from the stimulus; 2=immediate flinching or licking of the hind paw). The procedure was repeated 6 times and the average score was used as the analgesic reaction score.

The analgesic examination was conducted in a blind method. The person who conducted the experiment was visually able to distinguish the FENTANEST™ fentanyl citrate injection formulation from each emulsion, but he conducted the experiment without knowing the type of emulsion for each formulation. FIG. 1 shows the daily changes in pain-related score and paw volume for 20 days following the inoculation of melanoma cells to the plantar of hind paw. The hind paw inoculated with melanoma cells (ipsi) began to show an increase in pain-related score beginning on the $9^{th}$ day following inoculation. Pain-related score increased sharply on the $10^{th}$ day and continued until the onset of a plateau on the $15^{th}$ day. The analgesic examination was conducted on the $16^{th}$ day after inoculation of melanoma cells. Increases in pain-related score correlated well with increases in paw volume, which showed steady increase beginning on the $9^{th}$ day following inoculation. As a control, the hind paw that was not inoculated (contra.) showed no increase in pain-related score and hind paw volume remained constant through the duration of the 20 days following inoculation. FIG. 1 also shows the error bars associated with measurements for each day.

B. Results

Summary

The hind paw inoculated with melanoma cells (ipsi.) showed a dose dependent decrease in pain-related score that peaked at 15 minutes after intravenous administration of FENTANEST™ fentanyl citrate injection formulation (FIG. 2) and Fentanyl Emulsion A (FIG. 3) and the effects were observed for about 60 minutes. A significant inhibition was observed with 16 μg/kg and 48 μg/kg dosages, and sufficient effects were observed in the 48 μg/kg dosage group. A less significant inhibition with effects lasting only 30 minutes was observed in the group with 4.8 μg/kg dosage (FIGS. 2 and 3). The contralateral (cont.) hind paw showed no effects from injections at all dosages (FIG. 2). Injections in the absence of fentanyl (vehicle only) also showed no effects on pain-related score (FIG. 3). Measurements for pain-related score were an average from 6 independent trials.

Comparison of Inhibiting Effects After Administering Fentanyl or Formulations

Comparing the inhibiting effects at 15 minutes after administration, no significant difference was observed (FIGS. 2 and 3). However, compared with the reference standard, substantial inhibiting effects were observed for fentanyl emulsion A formulation (FIG. 3).

Comparing the inhibiting effects at 30 minutes after administration, no significant difference was observed (FIGS. 2 and 3). However, compared with the reference standard, lasting effects were observed for fentanyl emulsion A formulation (FIG. 3).

III. Assessment of Central Nervous System Mediated Side Effects of Fentanyl Emulsion Formulation A. Straub's Tail Reaction When mice are given opioids, their tails stand and trend rostrally. This reaction is called Straub's tail and may be mediated by the central nervous system, especially spinal cord. FENTANEST™ fentanyl citrate injection formulation induced Straub's tail reaction in all mice tested at higher doses (Table 3). The incidence of Straub's tail reaction was relatively low after injection of fentanyl emulsion A (Table 3). Similar results were observed in the duration of the Straub's tail reaction (FIG. 4).

TABLE 3

Straub's Tail Response Induced by Fentanyl Preparations

| Concentration (µg/ml) | Observed | Responder (%) FENTANEST ™ fentanyl citrate injection formulation | Responder (%) Fentanyl Emulsion A |
| --- | --- | --- | --- |
| 0 | 6 | 0 (0) | 0 (0) |
| 10 | 6 | 3 (50) | 2 (33) |
| 30 | 6 | 5 (83) | 2 (33) |
| 50 | 6 | 6 (100) | 4 (80) |

B. Locomotor Activity Effect

Figure 5:
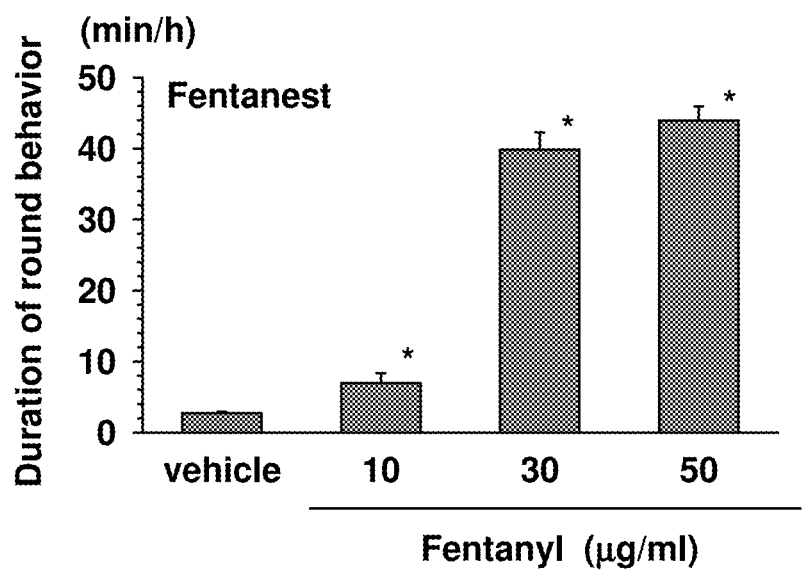
FIG. 5 shows one-direction locomotor activity induced by FENTANEST™ fentanyl citrate injection formulation. FENTANEST™ fentanyl citrate injection formulation and vehicle were administered intravenously in a volume of 0.10 ml. Results shown are mean±SEM of six animals. *p<0.05 (Dunnett's multiple comparisons).
Figure 6:
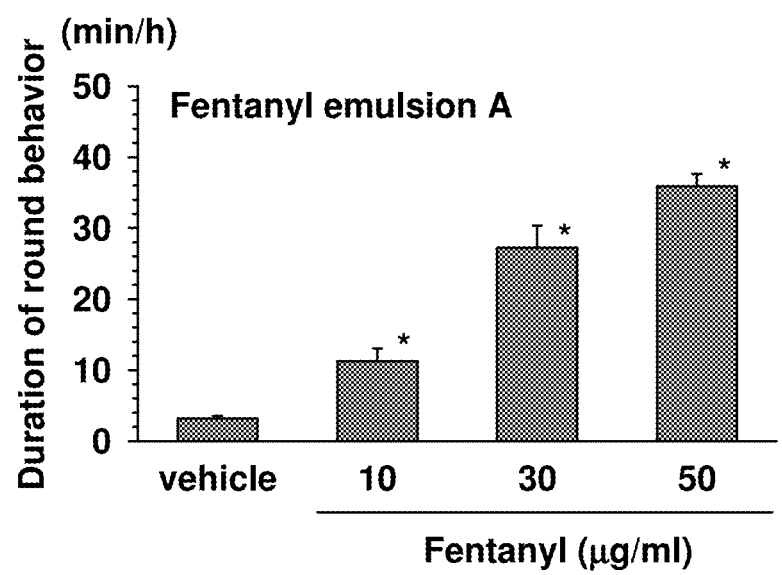
FIG. 6 shows one-direction locomotor activity induced by fentanyl emulsion A. Fentanyl emulsion A and vehicle were administered intravenously in a volume of 0.10 ml. Results shown are mean±SEM of six animals. *p<0.05 (Dunnett's multiple comparisons).

When mice are given high doses of opioids, locomotor activity is increased through the action on the central nervous system. FENTANEST™ fentanyl citrate injection formulation markedly increased locomotor activity at high concentrations of 30 and 50 µg/ml, but had no effect at a concentration of 10 µg/ml (FIG. 5). The increase of locomotor activity after fentanyl emulsion A was lower than that of FENTANEST™ fentanyl citrate injection formulation (FIG. 6). The effects of FENTANEST™ fentanyl citrate injection formulation and fentanyl emulsion A were compared as shown in FIG. 7. When compared with FENTANEST™ fentanyl citrate injection formulation, fentanyl emulsion A did resulted in significantly less locomotor activity at the concentration of 30 and 50 µg/ml.

C. Discussion

Since Straub's tail reaction and increased locomotor activity may be mainly mediated by the central nervous system, the central nervous system mediated side effects of fentanyl preparations were considered from the results. As compared to FENTANEST™ fentanyl citrate injection formulation, the central nervous system mediated side effects of fentanyl emulsion A were less severe than that of FENTANEST™ fentanyl citrate injection formulation.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An emulsion formulation comprising:
   0.1-10 mg/ml fentanyl;
   0.05-200 mg/ml Vegetable oil;
   water;
   0.1-50 mg/ml natural phospholipid as surfactant;
   oleic acid as emulsification enhancer; and
   a stabilizing agent.

2. The emulsion formulation according to claim 1, wherein said surfactant is chosen from egg-yolk phospholipid or soybean phospholipid.

3. The emulsion formulation according to claim 1, wherein said stabilizing agent is glycerin.

4. The emulsion formulation according to claim 1, wherein said emulsion formulation exhibits comparable efficacy as compared to a FENTANEST™ fentanyl citrate injection formulation.

5. The emulsion formulation according to claim 1, wherein said emulsion formulation exhibits reduced central nervous system mediated side effects as compared to a FENTANEST™ fentanyl citrate injection formulation.

6. A kit comprising an emulsion formulation comprising:
   0.1-10 mg/ml fentanyl;
   0.05-200 mg/ml Vegetable oil;
   water;
   0.1-50 mg/ml natural phospholipid as surfactant;
   oleic acid as emulsification enhancer; and
   a stabilizing agent.

7. The kit according to claim 6, wherein said surfactant is chosen from egg-yolk phospholipid or soybean phospholipid.

8. The kit according to claim 6, wherein said stabilizing agent is glycerin.

9. The kit according to claim 6, wherein said emulsion formulation exhibits comparable efficacy as compared to a FENTANEST™ fentanyl citrate injection formulation.

10. The kit according to claim 6, wherein said emulsion formulation exhibits reduced central nervous system mediated side effects as compared to a FENTANEST™ fentanyl citrate injection formulation.

11. The emulsion formulation according to claim 1, wherein said fentanyl is present in an amount ranging from 0.1 to 1 mg/ml.

12. The kit according to claim 6, wherein said fentanyl is present in an amount ranging from 0.1 to 1 mg/ml.

* * * * *